United States Patent
Yugawa et al.

(10) Patent No.: US 6,773,564 B1
(45) Date of Patent: Aug. 10, 2004

(54) GLUCOSE SENSOR

(75) Inventors: Keiko Yugawa, Nara (JP); Toshihiko Yoshioka, Hirakata (JP); Shiro Nankai, Hirakata (JP); Junko Iwata, Ehime (JP); Shoji Miyazaki, Matsuyama (JP); Hideyuki Baba, Matsuyama (JP); Seiji Takeshima, Tsuruga (JP)

(73) Assignees: Matsushita Electric Industrial Co., Ltd., Osaka (JP); part interest; Toyobo Co., Ltd., Osaka (JP); part interest ( * ) Notice: Subject to any disclaimer, the term of this patent is extended or adjusted under 35 U.S.C. 154(b) by 0 days.

(21) Appl. No.: 09/406,832

(22) Filed: Sep. 28, 1999

(30) Foreign Application Priority Data

Sep. 29, 1998 (JP) .......................................... 10-276153
Jul. 27, 1999 (JP) .......................................... 11-212703

(51) Int. Cl.[7] ........................ G01N 27/327; C12Q 1/54; C12N 9/04
(52) U.S. Cl. ..................... 204/403.14; 435/14; 435/190
(58) Field of Search .......................... 204/403, 403.01, 204/403.04, 403.09, 403.1, 403.11, 403.12, 403.14; 435/14, 189, 190; 205/777.5

(56) References Cited

U.S. PATENT DOCUMENTS

| | | | |
|---|---|---|---|
| 4,545,382 A | | 10/1985 | Higgins et al. |
| 4,711,245 A | | 12/1987 | Higgins et al. |
| 5,334,508 A | | 8/1994 | Hoenes |
| 5,378,628 A | | 1/1995 | Gratzel et al. .............. 435/288 |
| 5,424,204 A | * | 6/1995 | Aoyama et al. ............ 435/188 |
| 5,466,575 A | | 11/1995 | Cozzette et al. |
| 5,554,339 A | | 9/1996 | Cozzette et al. |
| 5,682,884 A | | 11/1997 | Hill et al. |
| 5,762,770 A | | 6/1998 | Pritchard et al. |
| 5,804,047 A | | 9/1998 | Karube et al. .............. 204/403 |
| 5,820,551 A | | 10/1998 | Hill et al. |
| 5,997,817 A | * | 12/1999 | Crismore et al. ............. 422/58 |
| 6,025,203 A | * | 2/2000 | Vetter et al. ................ 436/170 |
| 6,071,391 A | * | 6/2000 | Gotoh et al. ................ 204/403 |
| 6,077,660 A | * | 6/2000 | Wong et al. .................... 435/4 |
| 6,270,637 B1 | | 8/2001 | Crismore et al. |

FOREIGN PATENT DOCUMENTS

| | | |
|---|---|---|
| EP | 0 357 027 | 8/1989 |
| EP | 872728 A1 | 10/1998 |
| JP | 09140378 | * 6/1997 |
| JP | 10-227755 | 8/1998 |

OTHER PUBLICATIONS

CAPLUS abstract of Maslinska–Solich ("Maleic anhydride copolymers in clinical analysis," Chemia Stosowana (1990), 34(1–2), (11–22).*
First page of "Collidine" entry in online Wiley Enchclopedia of Reagetns for Organic Synthesis.*
First page of "Colicins" entry in online Wiley Encyclopedia of Molecular Biology.*
First page of "Bacteriocins" entry in online Wiley Encyclopedia of Molecular Biology.*
JAPIO abstract of JP09140378.*
CAPLUS abstract of Cucinotta et al. ("three–dimensional cyclodextrin: a new class of hosts by trehalose capping of beta–cyclodextrin", J. Inclusion Phenom. Mol. Recognit. Chem. (1996), 25(1–3), 39–42).*

(List continued on next page.)

Primary Examiner—Alex Noguerola
(74) Attorney, Agent, or Firm—McDermott, Will & Emery

(57) ABSTRACT

The present invention provides a high performance glucose sensor which can demonstrate high stability against preservation and produces only a low blank value. The glucose sensor comprises an electrically insulating base plate, an electrode system formed on the base plate, and a reaction layer which is formed in contact with or in the vicinity of the electrode system and contains at least a glucose dehydrogenase whose coenzyme is pyrrolo-quinoline quinone, the reaction layer further containing an additive such as phthalic acid.

80 Claims, 7 Drawing Sheets

OTHER PUBLICATIONS

CAPLUS abstract of Takahashi et al. ("Effect of a trehalose inhibitor, validoxylamine A, on three species of flies", Appl. Entomol. Zool. (1995), 30(1), 231–9).*

Victor L. Davidson, "Principles and Applications of Quinoproteins," 1993 pp. 47–63.

R.K. Poole, "Microbial Physiology," vol. 40, pp. 4–80.

Biotechnologies Techniques, vol. 11, No. 8, 1997, pp. 577–680 Preparation of Iyophilized Pyrroloquinoline Quinone Glucose Dehydrogenase Using Trehalose as an Additive, month unknown.

Hiromi Yoshida and Koji Sode, Thr424 to Asn Substitution Alters Bivalent Metal Specificity of Pyrroloquinoline Quinone Glucose Dehydrogenase, 1997, J. Biochem. Mol. Biol. & Biophys., vol. 1, pp. 89–93, month unknown.

Arief Budi Witarto, Shokichi Oh–Uchi, Mitsuaki Narita, and Koji Sode, Secondary Structure Study of Pyrroloquinoline Quinone Glucose Dehydrogenase, 1999, J. Biochem. Mol. Biol. & Biophys., vol. 1, pp. 209–213, month unknown.

Koji Sode and Hiroyuki Sano, Glu742 Substitution to Lys Enhances The EDTA Tolerance of *Escherichia Coli* PQQ Glucose Dehydrogenase, 1994, Biotechnology Letters, vol. 16, No. 5, pp. 455–460, month unknown.

Arief Budi Witarto, Takafumi Ohtera, and Koji Sode, Site–Directed Mutagenesis Study on the Thermal Stability of a Chimeric PQQ Glucose Dehydrogenase and Its Structural Interpretation, 1999, Applied Biochemistry and Biotechnology, vol. 77–79, pp. 159–168.

Marcel Dekker, Inc., Oxygen Insensitive Glucose Biosensor Based on PQQ–Dependent Glucose Dehydrogenase, 1999, Analytical Letters, vol. 32(2), pp. 299–316, month unknown.

Kazunobu Matsushita, Hirohide Toyama, Minoru Ameyama, Osao Adachi, Aster Dewanti, and Johannis A. Duine, 1995, Biosci. Biotech. Biochem, vol. 59(8), pp. 1548–1555, month unknown.

Kazunobu Matsushita, Yasue Ohno, Emido Shinagawa, Osao Adachi, and Minoru Ameyama, 1980, Agric. Biol. Chem, vol. 44(7), pp. 1505–1512, month unknown.

Minoru Ameyama, Masatsugu Nonobe, Emiko Shinagawa, Kazunobu Matsushita, Koichi Takimoto, and Osao Adachi, 1986, Agric. Biol. Chem., vol. 50(1), pp. 49–47, month unknown.

Minoru Ameyana, Emiko Shinagawa, Kazunobu Matsushita, and Osao Adachi, D–Glucose Dehydrogenase of Gluconobacter suboxydans: Soubilization, Purification and Characterization, 1981, Agric. Biol. Chem., vol. 45(4), pp. 851–861, month unknown.

Jens G. Hauge, Glucose Dehydrogenase of Bacterium anitratum: an Enzyme with a Novel Prosthetic Group, 1964, vol. 239, No. 11, pp. 3630–3639, month unknown.

Tokuji Ikeda, Hiroshige Matsubara, Kan Kato, Dyah Iswantini, Kenji Kano, Mamoru Yamada, Electrochemical Monitoring of In Vivo Reconstitution of Glucose Dehydrogenase in *Escherichia Coli* cells With Externally Added Pyrroloquinoline Quinone, 1998, Journal of Electroanalytical Chemistry, vol. 449, pp. 219–224, month unknown.

E.J. D'Costa, I.J. Higgins and A.P.F. Turner, Quinoprotein Glucose Dehydrogenase and its Application in an Amperometric Glucose Sensor, 1986, Biosensors, vol. 2, pp. 71–87, month unknown.

Koji Sode and Hiromi Yoshida, Construction and Characterization of a Chimeric *Escherichia Coli* PQQ Glucose Dehydrogenase (PQQGHD) with Increased EDTA Tolerance, 1997, Denki Kagaku, vol. 65, No. 6, pp. 449–451.

Tomohiko Yamazaki, Wakako Tsugawa, and Koji Sode, Increase Thermal Stability of Glucose Dehydrogenase by Cross–Linking Chemical Modification, 1999, Biotechnology Letters, vol. 21, pp. 199–202, month unknown.

Koji Sode, Miki Shirahane, and Hiromi Yoshida, Construction and Characterization of A Linked–Dimeric Pyrroloquinoline Quinone Glucose Dehydrogenase, 1999, Biotechnology Letters, vol. 21, pp. 707–710, month unknown.

Koji Sode, Tomonori Shimakita, Shokichi Ohuchi, and Tomohiko Yamazaki, Stablization of Pyrroloquinoline Quinone Glucose Dehydrogenase By Cross–Linking Chemical Modification, 1996, Biotechnology Letters, vol. 18, No. 9, pp. 997–1002.

Koji Sode and Nozomu Yasutake, Preparation of Lyophilized Pyrroloquinoline Quinone Glucose Dehydrogenase Using Trehalose As An Additive, 1997, Biotechnology Techniques, vol. 11, No. 8, pp. 577–580, month unknown.

Koji Sode, Arief Budi Witarto, Kazumoto Watanabe, Keisuke Noda, Shunsuke Ito and, Wakako Tsugawa, Over Expression of PQQ Glucose Dehydrogenase in *Escherichia Coli* Under Holo Enzyme Forming Condition, 1994, vol. 16, No. 12, pp. 1265–1268, Dec.

Koji Sode, Hiromi Yoshida, Kazunori Matsumura, Tomoko Kikuchi, Mika Watanabe, Nozomo Yasutake, Shunsuke Ito and Hiroyuki Sano, Elucidation of The Region Responsible For Edta Tolerance In PQQ Gluccose Dehydrogenases By Construction *Escherichia Coli* and Acinetobacter Calcoaceticus Chimeric Enzymes, 1995, Biochemical and Biophysical Research Communications, vol. 211, No. 1, pp. 268–273, Jun.

Koji Sode, Wakako Tsugawa, Tomohiko Yamazaki, Masato Watanabe, Nobuhiro Ogasawara, and Mitsuharu Tanaka, A Novel Thermostable Glucose Dehydrogenase Varying Temperature Properties By Altering Its Quaternary Structures, 1996, Enzyme and Microbial Technology, vol. 19, pp. 82–85, month unknown.

Koji Sode, Kazumoto Watanabe, Shunsuke Ito, Kazunori Matsumura, Tomoko Kikuchi, Thermostable Chimeric PQQ Glucose Dehydrogenase, 1995, Federation of European Biochemical Societies Letters, vol. 364, pp. 325–327, month unknown.

Koji Sode, Koji Ito, Arief Budi Witarto, Kazumoto Watanabe, Hiromi Yoshida, Pieter Postma, Increased Production of Recombinant Pyrroloquinoline Quinone (PQQ) Glucose Dehydrogenase By Metabolically Engineered *Escherichia Coli* Strain Capable of PQQ Biosynthesis, 1996, Journal of Biotechnology, pp. 239–243, month unknown.

Koji Sode, Sayaka Sugimoto, Mika Watanabe, Wakako Tsugawa, Effect of PQQ Glucose Dehydrogenase Overexpression In *Escherichia Coli* On Sugar–Dependent Respiration, 1995, Journal of Biotechnology, vol. 43, pp. 41–44, month unknown.

Arjen J.J. Olsthoorn, Tetsuo Otsuki and Johannis A. Duine, Negative Cooperativity In The Steady–State Kinetics of Sugar Oxidation By Soluble Quinoprotein Glucose Dehydrogenase From Acinetobacter Calcoaceticus, 1998, eur. J. Biochem, pp. 255–261, month unknown.

Ling Ye, Martin Hammerle, Arjen J.J. Olsthoorn, Wolfgang Schuhmann, Hans–Ludwig Schmidt, Johannis A. Duine, and Adam Heller, High Current Density "Wired" Quinoprotein Glucose Dehydrogenase Electrode, 1993, Analytical Chemistry, vol. 65, No. 3, pp. 238–241, Feb.

Hiromi Yoshida, Katsuhiro Kojima, Arief Budi Witarto and Koji Sode, Engineering a Chimeric Pyrroloquinoline Quinone Glucose Dehydrogenase: improvement of EDTA tolerance, thermal stability and substrate specificity, 1999, Protein Engineering, vol. 12, No. 1, pp. 63–70, month unknown.

K. Sode and K. Kojima, Improved Substrate Specificity and Dynamic Range For Glucose Measurement of *Escherichia Coli* PQQ Glucose Dehydrogenase By Site Directed Mutagenesis, 1997, Biotechnology Letters, vol. 19, No. 11, pp. 1073–1077, month unknown.

Tomohiko Yamazaki, Wakako Tsugawa, and Koji Sode, Subunit Analyses of a Novel Thermostable Glucose Dehydrogenase Showing Deifferent Temperature Properties According to Its Quaternary Structure, Applied Biochemistry and Biotechnology, vol. 77–79, pp. 325–335, month unknown.

Paul Dokter, John E. Van Wielink, Mario A.G. Van Kleef and Johannis A. Duine, Cytochrome b–562 from Acinetobacter Calcoaceticus L.M.D. 79.41, 1988, Biochem J., vol. 254, pp. 131–138, month unknown.

Koji Sode, Kazunori Matsumura, Wakako Tsugawa, and Mitsuharu Tanaka, Isolation of a Marine Bacterial Pyrroloquinoline Quinone–Dependent Glucose Dehydrogenase, 1995, J. Mar. Biotechnol, vol. 2, pp. 214–218, month unknown.

A. Geerlof, P. Dokter, J.E. van Wielink and J.A. Duine, Haem–Containing Protein Complexes of Acinetobacter Calcoaceticus As Secondary Electron Acceptors for Quinoprotein Glucose Dehydrogenase, 1989, Antonie van Leeuwenhoek, vol. 56, pp. 81–84, month unknown.

Wen Jin, Ulla Wollenberger and Frieder W. Scheller, PQQ as Redox Shuttle for Quinoprotein Glucose Dehydrogenase, 1998, Biol. Chem., vol. 379, pp. 1207–1211, month unknown.

Jens G. Hauge, Kinetics and Specificity of Glucose Dehydrogenase From Bacterium Anitratum, 1960, Biochim. biophys. Acta, vol. 45, pp. 263–269, month unknown.

Arthur Oubrie, Henriette J. Roseboom, Kor H. Kalk, Johannis A. Duine and Bauke W. Dijkstra, The 1.7 A Crystal Structure of the Apo Form of the Soluble Quinoprotein Glucose Dehydrogenase from Acinetobacter calcoacetus Reveals a Novel Internal Conserve Sequence Repeat, 1999, vol. 289, pp. 319–333, month unknown.

Jens G. Hauge, Purification and Properties of Glucose Dehydrogenase and Cytochrome b from Bacterium Anitratum, 1960, Biochim. Biophys. Acta, vol. 45, pp. 250–262, month unknown.

Matthias Wanner, Torsten Sixt, Karl–Wilhelm Klinkhammer, and Woflgang Kaim, First Experimental Structure of a 1:1 Metal Complex with a PPQ Cofactor Derivative Ouside Dehydrogenase Enzymes, 1999, Inorganic Chemistry, vol. 38, No. 11, pp. 2753–2755, month unknown.

Asteriani R. Dewanti and Johannis A. Duine, Reconstitution of Membrane –Integrated Quinoprotein Glucose Dehydrogenase Apoenzyme with PQQ and the Holoenzyme's Mechanism of Action, 1998, Biochemistry, vol. 37, No. 19, pp. 6810–6818, month unknown.

M. Alkasrawi, I.C. Popescu, V. Laurinavicius, B. Mattiasson and E. Csoregi, A Redox Hydrogel Integrated PQQ–Glucose Dehydrogenase Based Glucose Electrode, 1999, Anal. Communication, vol. 36, pp. 395–398, month unknown.

Juan–R. Mor and Rocco Guarnaccia, Assay of Glucose Using an Electrochemical Enzymatic Sensor, 1977, Analytical Biochemistry, vol. 79, pp. 319–328, month unknown.

J.A. Duine, J. Frank and J.K. Van Zeeland, Glucose Dehydrogenase From Acinetobacter Calcoaceticus, FEBS Letters, 1979, vol. 108, No. 2, pp. 443–446, Dec.

Dyah Iswantini, Kan Kato, Kenji Kano, Tokuji Ikeda, Electrochemical Measurements of Glucose Dehydrogenase Activity Exhibited by *Escherichia Coli* Cells; Effects of the Additions of Pyrroloquinoline Quinone, Magnesium or Calcium Ions and Ethylenediaminetetraacetic Acid, 1998, Bioelectrochemistry and Bioenergetics, vol. 46, pp. 245–254, month unknown.

Kazunobu Matsushita, Emiko Shinagawa, Osao Adachi and Minoru Ameyama, Quinoprotein D–glucose Dehydrogenases in Acinetobacter Calcoaceticus LMD 79:41: Purification and Characterization of the Membrane–Bound Enzyme Distinct from the Soluble Enzyme, 1989, Antonie van Leeuwenhoek, vol. 56, pp. 63–72, month unknown.

Gyles E. Cozier and Christopher Anthony, Structure of the Quinoprotein Glucose Dehydrogenase of *Escherichia Coli* Modelled on that of Methanol Dehydrogenase from Methylobacterium Extorquens, 1995, Biochem. J., vol. 312, pp. 679–685, month unknown.

* cited by examiner

GLUCOSE SENSOR

BACKGROUND OF THE INVENTION

The present invention relates to a glucose sensor which facilitates rapid and simplified quantitative analysis of a specific component contained in a sample with high accuracy. More specifically, the present invention relates to a method for stabilizing glucose dehydrogenase whose coenzyme is pyrrolo-quinoline quinone and a glucose dehydrogenase composition obtained by the stabilizing method.

Conventionally, a variety of biosensor have been proposed as a system facilitating simple quantitation of a specific component contained in a sample solution without requiring dilution or agitation of a sample solution. The following is a known example of such biosensor (Japanese Laid-Open Patent Publication No. Hei 2-062952).

The blosensor disclosed in this prior art is produced by the steps of forming an electrode system including a working electrode, a counter electrode and a reference electrode on an electrically insulating base plate using a known screen printing method or the like and subsequently forming immediately on this electrode system an enzyme reaction layer containing a hydrophilic polymer, an oxidoreductase, and an electron acceptor.

Upon a dropwise addition of a sample solution containing a substrate over the enzyme reaction layer of the biosensor thus produced, the enzyme reaction layer dissolves in the sample solution and the substrate in the sample solution is oxidized by the enzyme. At that time, the electron acceptor is reduced. After enzyme reaction is completed, the reduced electron acceptor is electrochemically reoxidized. The concentration of the substrate in the sample solution can be determined based on the oxidation current produced by the reoxidation reaction.

In principle, the biosensor as described above permits measurements of various materials if a suitable enzyme corresponding to the substrate of an analyte is selected.

For example, if glucose oxidase is the selected enzyme, then a glucose sensor for measuring a glucose concentration in the sample solution can be obtained.

The biosensor of the above structure normally accommodates the enzyme in the dried state. However, the enzyme is susceptible to degeneration when exposed to water in air for a long time, because it is essentially composed of protein which is readily degraded. In the extreme, the enzyme is exposed to a risk of losing the enzyme activity.

Therefore, long-term preservation of sensors after their production may result in a loss of activity of the enzyme and a depletion of necessary enzyme for reacting with the substrate. This may lead to a noncommensurable sensor response current to the substrate concentration.

In general, introduction of a sample solution containing a 0% substrate can produce some degree of sensor response current (hereinafter referred to as "blank value"). One cause of such blank value may be induction of electrode reaction due to an accumulation of ions contained in the sample solution dissolving the reaction layer on the surface of the electrode system formed on the base plate. A large blank value can serve as a factor for impairing the correlation between response current and substrate concentration, rendering it impossible to make precise quantitative analysis of the substrate.

Therefore, securing an environment where the enzyme can retain the enzyme activity for a long term in the vicinity of the enzyme is key to the provision of a biosensor demonstrating excellent stability against preservation and producing a low blank value. It is also important to secure an environment, which produces a minimal and negligible blank value, around the surface of the electrode system on the base plate. It is also necessary to realize smooth transfer of both electron and substrate during enzyme reaction so as to enhance sensor response.

One conventional countermeasure for solving the above-mentioned problems is an inclusion of an additive such as phosphoric acid in the reaction layer.

In order to produce a high performance glucose sensor, on the other hand, glucose dehydrogenase whose coenzyme is pyrrolo-quinoline quinone (hereinafter abbreviated to "PQQ-GDH") has conventionally been used as the enzyme. If PQQ-GDH is included as the enzyme, the resultant glucose sensor inherently has a characteristic feature of complete freedom from any adverse influence of dissolved oxygen in blood or the like on the enzyme reaction, because oxygen plays no role in the catalytic action of PQQ-GDH. Therefore, measurement values obtained from such glucose sensor are also free of variations due to oxygen partial pressure in the sample solution. This means that a high performance sensor will result from the use of PQQ-GDH as the enzyme.

However, the use of PQQ-GDH as the enzyme has a drawback that even inclusion of an additive such as phosphoric acid as exemplified before in the reaction layer can not help the resultant biosensor to lower the blank value sufficiently and to demonstrate sufficiently high stability against preservation.

BRIEF SUMMARY OF THE INVENTION

In view of the above-mentioned problems, a primary object of the present invention is to provide a high performance glucose sensor demonstrating high stability against preservation and producing a low blank value. Other objects of the present invention are to provide a method for stabilizing PQQ-GDH and a glucose dehydrogenase composition obtained by the stabilizing method.

The glucose sensor in accordance with the present invention comprises an electrically insulating base plate, an electrode system including at least a working electrode and a counter electrode formed on the base plate, and a reaction layer which is formed in contact with or in the vicinity of the electrode system and contains at least PQQ-GDH, wherein the reaction layer further contains at least one additive selected from the group consisting of phthalic acid, a phthalate, maleic acid, a maleate, succinic acid, a succinate, triethanol amine, a triethanol amine salt, citric acid, a citrate, dimethyl glutaric acid, 2-(N-morpholino)ethane sulfonic acid, a 2-(N-morpholino)ethane sulfonate, tris (hydroxymethyl)glycine, a tris(hydroxymethyl)glycine salt, tris(hydroxymethyl)aminomethane, a tris(hydroxymethyl) aminomethane salt, imidazole, and collidine.

In a preferred mode of the present invention, the enzyme is coated with the additive.

The present invention also relates to a method for stabilizing glucose dehydrogenase for use in glucose sensors, wherein at least one additive is added to PQQ-GDH, the additive being selected from the group consisting of phthalic acid, a phthalate maleic acid, a maleate, succinic acid, a succinate, triethanol amine, a triethanol amine salt, citric acid, a citrate, dimethyl glutaric acid, 2-(N-morpholino) ethane sulfonic acid, a 2-(N-morpholino)ethane sulfonate, tris(hydroxymethyl)glycine, a tris(hydroxymethly)glycine salt, tris(hydroxymethyl)aminomethane, a tris (hydroxymethyl)aminomethane salt, imidazole, and collidine.

The present invention further relates to a glucose dehydrogenase composition for use in glucose sensors, the composition containing PQQ-GDH and at least one additive selected from the group consisting of phthalic acid, a phthalate, maleic acid, a maleate, succinic acid, a succinate, triethanol amine, a triethanol amine salt, citric acid, a citrate, dimethyl glutaric acid, 2-(N-morpholino)ethane sulfonic acid, a 2-(N-morpholino)ethane sulfonate, tris (hydroxymethyl)glycine, a tris(hydroxymethyl)glycine salt, tris(hydroxymethyl)aminomethane, a tris(hydroxymethyl) aminomethane salt, imidazole, and collidine.

In an aspect of the invention, the glucose sensor comprises an electrically insulating base plate, an electrode system including at least a working electrode and a counter electrode formed on said base plate, and a reaction layer which is formed in contact with or in the vicinity of said electrode system. The reaction layer contains: at least one stabilizer selected from the group consisting of a metal salt, an organic acid, a protein, and a sugar and a derivative thereof; a glucose dehydrogenase whose coenzyme is pyrrolo-quinoline quinone; and a buffer.

In another aspect of the invention, the method for stabilizing glucose dehydrogenase for use in glucose sensors includes adding a stabilizer and a buffer to glucose dehydrogenase whose coenzyme is pyrrolo-quinoline quinone.

In yet another aspect of the invention, a glucose dehydrogenase composition for use in glucose sensors contains: at least one stabilizer selected from the group consisting of a metal salt, an organic acid, a protein, and a sugar and a derivative thereof; a glucose dehydrogenase whose coenzyme is pyrrolo-quinoline quinone; and a buffer.

The buffer is selected from the group consisting of maleic acid, a maleate, succinic acid, a succinate, triethanol amine, a triethanol amine salt, citric acid, a citrate, dimethyl glutaric acid, 2-(N-morpholino)ethane sulfonic acid, a 2-(N-morpholino)ethane sulfonate, tris(hydroxymethyl)glycine, a tris(hydroxymethyl)glycine salt, tris(hydroxymethyl) aminomethane, a tris(hydroxymethyl)aminomethane salt, imidazole or colicin.

The stabilizer can be a metal salt selected from the group consisting of a calcium salt, $CaCl_2$, a strontium salt and a manganese salt; an organic acid selected from the group consisting of α-ketoglutaric acid, malic acid, fumaric acid, gluconic acid, cholic acid and deoxycholic acid; a protein selected from the group consisting of bovine serum albumin, egg albumin and gelatin; a sugar or a derivative thereof selected from the group consisting of a monosaccharide and a derivative thereof, a disaccharide, and a derivative thereof, an oligosaccharide and a derivative thereof, and a polysaccharide and a derivative thereof; a monosaccharide selected from the group consisting of glucose, fructose, galactose, mannose, xylose, inositol, monnitol, sorbitol, ribitol, glucosamine and deoxyglucose, or a derivative thereof; a disaccharide selected from the group consisting of sucrose, lactose, maltose and trehalose, or a derivative thereof; an oligosaccharide selected from the group consisting of malt triose, maltosyl cyclodextrin, α-cyclodextrin, β-cyclodextrin and γ-cyclodextrin, or a derivative thereof; a polysaccharide selected from the group consisting of dextrin, amylose, glycogen, inulin and Ficoll, or a derivative thereof.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
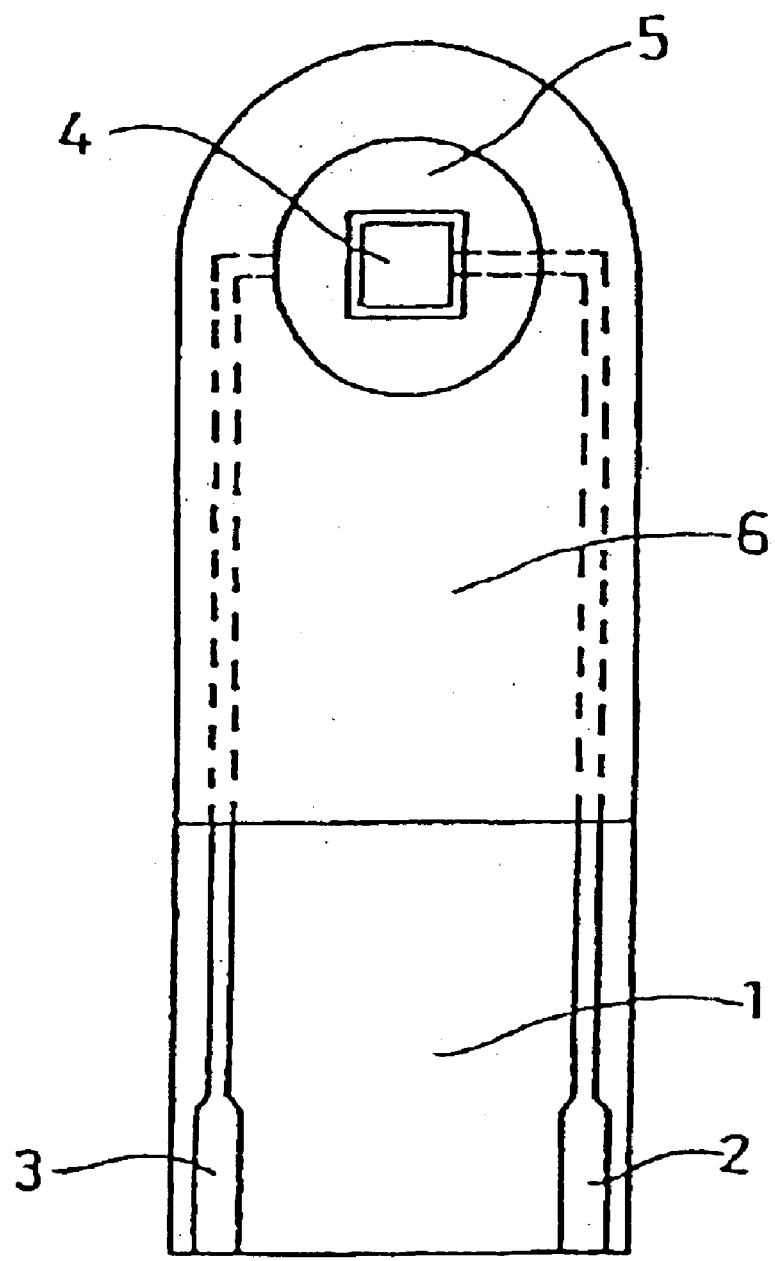
FIG. 1 is a schematic plan view illustrating a glucose sensor in accordance with one example of the present invention from which the reaction layer has been omitted.

As noted above, the glucose sensor in accordance with the present invention further contains an additive such as phthalic acid in the reaction layer containing PQQ-GDH as the enzyme.

When the reaction layer is formed by dropping and drying an aqueous mixed solution of PQQ-GDH with the additive such as hydrogen potassium phthalate, for example, the surface of the enzyme PQQ-GDH is coated with the additive hydrogen potassium phthalate. Such coating protects the enzyme from any change in the environmental conditions such as temperature, humidity, electric charge. As a result, the enzyme can retain stable enzyme activity for a long term.

Furthermore, upon introduction of a sample solution into the sensor, the additive is dissolved in the sample solution and ionized. The ionized additive in turn influences preexisting ions in the sample solution and those produced upon dissolution of the reaction layer in the sample solution. As a result, those ions can not stay on the surface of the electrode system on the base plate, which contributes to minimizing the blank value.

The presence of such additive in the reaction layer is also technically advantageous in that it helps dissolution of the reaction layer in water, which facilitates immediate dissolution of the reaction layer in the sample solution upon addition of the sample solution to the reaction layer, thereby enabling smooth progress of both enzyme reaction and electrode reaction.

The additive from which the above-mentioned effects can be expected may be exemplified as phthalic acid, a phthalate such as potassium hydrogen phthalate, maleic acid, a maleate such as sodium maleate, succinic acid, a succinate such as sodium succinate, triethanol amine, a triethanol amine salt such as triethanol amine hydrochloride, citric acid, a citrate such a monopotassium citrate, calcium citrate, tripotassium citrate, trisodium citrate, trilithium citrate, diammonium hydrogen citrate, disodium hydrogen citrate, sodium citrate, diammonium citrate, potassium dihydrogen citrate, sodium dihydrogen citrate, disodium citrate or magnesium citrate, dimethyl glutaric acid, (2-N-morpholino)ethane sulfonic acid, a 2-(N-morpholino)ethane sulfonate, tris (hydroxymethyl)glycine, a tris(hydroxymethyl)glycine salt, tris(hydroxymethyl)aminomethane, a tris(hydroxymethyl) aminomethane salt such as tris(hydroxymethyl) aminomethane hydrochloride, imidazole, and collidine.

Particularly, the use of potassium hydrogen phthalate as the additive produces a glucose sensor exhibiting excellent stability against preservation and superb response characteristics with a very low blank value.

All of the above exemplified additives are compounds which can serve as buffers. At use, they can be adjusted to a desired pH using an acid such as hydrochloric acid, acetic acid or an alkali such as sodium hydroxide, potassium hydroxide if occasion demands. A preferred pH range is 5.0 to 8.5. Those additives may be dissolved in other appropriate buffer solutions at use.

The ratio of the additive may be in a range of 5 to 80 $\mu$M per 250 to 10,000 U (=units)/ml of PQQ-GDH. From the aspects of stability and blank value, namely, due to the reason that excess content of the additive decreases specific activity of the enzyme, a preferred ratio of the additive should be in a range of 10 to 50 $\mu$M.

According to the present invention, the reaction layer may further contain such electron acceptor that is reduced by enzyme reaction. Applicable electron acceptor for this purpose may be exemplified as ferricyanide ion, p-benzoquinone and a derivative thereof, phenazine methosulphate, methylene blue, ferrocene and a derivative thereof, and the like.

According to the present invention, the reaction layer may further include a hydrophilic polymer. The presence of a hydrophilic polymer in the reaction layer prevents separation or dissection of the reaction layer from the surface of the electrode system. The hydrophilic polymer also has a preventive effect against crack development on the surface of the reaction layer, thereby enhancing the reliability of the resultant biosensor.

Preferred examples of hydrophilic polymer for this purpose include carboxymethyl cellulose, hydroxyethyl cellulose, hydroxypropyl cellulose, methyl cellulose, ethyl cellulose, ethylhydroxyethyl cellulose, carboxymethylethyl cellulose, polyvinyl pyrrolidone, polyvinyl alcohol, polyamine such as polylysine, polystyrene sulfonate, gelatin and a derivative thereof, a polymer of acrylic acid and its acrylate, a polymer of methacrylic acid and a methacrylate, starch and a derivative thereof, a polymer of maleic anhydride and a maleate, agarose gel and a derivative thereof.

The reaction layer may be located at various sites in the biosensor in addition to the location on the electrode system formed on the electrically insulating base plate unless the effects of the present invention would be lost. For example, the reaction layer may be located anywhere in the biosensor apart from the electrode system on the base plate. The biosensor in accordance with the present invention further comprises a cover member. The cover member is combined with the base plate to form, between the cover member and the base plate, a sample solution supply pathway for supplying a sample solution to the electrode system. The reaction layer may be located on an exposed side of the cover member to the sample solution supply pathway.

As to the measurement of oxidation current, there are two methods: one is a two-electrode system comprising only a working electrode and a counter electrode and the other is a three-electrode system further comprising a reference electrode in addition to the two electrodes. The latter facilitates more precise and accurate measurement.

As mentioned before, the present invention also relates to a method for stabilizing glucose dehydrogenase for use in glucose sensors by adding one of the above-exemplified additives to PQQ-GDH. The present invention does not limit the method of addition to particular one and any method can be applied unless it damages the effects of the present invention.

The present invention is also directed to a glucose dehydrogenase composition for use in glucose sensors that is composed of PQQ-GDH plus the additive.

The stabilized glucose dehydrogenase composition in accordance with the present invention may further contain other stabilizer to the extent not impairing the effects of the present invention, in addition to the above-mentioned additive.

Applicable examples of stabilizer for this purpose include a metal salt, a protein, an amino acid, a sugar, an organic acid, a surfactant and so on.

The metal salt may be exemplified as a halogenide or a halide of calcium, strontium or manganese, their sulfate or nitrate.

Preferred protein is one which does not have any adverse effect on the enzyme activity. Examples of such protein are bovine serum albumin (BSA), egg albumin and gelatin.

Applicable amino acid may be exemplified as glycylglycine and polylysine, in addition to general amino acids such as lysine, histidine and glutamic acid. Above all, a highly water-soluble amino acid is preferable.

As the sugar, any sugar may be used regardless of the species and may be exemplified as monosaccharide, disaccharide, oligosaccharide and polysaccharide. Their derivatives may also be applicable. More specific examples are glucose, fructose, galactose, mannose, xylose, sucrose, lactose, maltose, trehalose, malt triose, maltosyl cyclodextrin, $\alpha$-cyclodextrin, $\beta$-cyclodextrin, $\gamma$-cyclodextrin, dextrin, amylose, glycogen, starch, inulin, glucosamine, inositol, mannitol, sorbitol, ribitol and deoxyglucose.

Examples of organic acid include $\alpha$-ketoglutaric acid, malic acid, fumaric acid, gluconic acid, cholic acid, and deoxycholic acid.

Preferable surfactant is non-ionic one.

Among others, boric acid, borax, potassium chloride, sodium chloride, ammonium sulfate, glycerol, Ficoll, EDTA (ethylenediaminetetraacetic acid), EGTA, DTT (dithiothreitol), DTE (dithioerythritol), GSH (glutathione) or 2-mercaptoethanol may also be applicable.

A preferable amount range of those stabilizers is 0.0001 to 1.0 part by weight per 1.0 part by weight of glucose dehydrogenase.

The glucose dehydrogenase composition of PQQ-GDH added with, if necessary, the above-mentioned stabilizer in addition to the additive in accordance with the present invention has low cost and can retain its activity without adverse influence on the intrinsic property of the enzyme.

The coenzyme pyrrolo-quinoline quinone as adopted by the present invention may be derived from any source.

Now, the measurement method of the activity of PQQ-GDH of the present invention will be described.

The reagent used is a mixed reagent solution of 50 mM PIPES buffer solution, 0.2 mH PMS (pH 6.5), 0.2 mM NTB, 30.6 mM glucose and 0.19% Triton X-100.

After heating 3 ml of the mixed reagent solution at 37° C. for about 5 min, a PQQ-GDH solution was added to the heated mixed reagent solution at 0.1 ml and the resultant solution was gently stirred.

Subsequently, the solution thus obtained was measured for its absorbance using a spectrophotometer at a controlled temperature of 37° C. and the absorbance was recorded for 5 minutes. Water was used as control. Then, changes in absorbance per min was calculated from a linear portion on the recorded spectral data. Double blind test was made by measuring absorbance of the mixed reagent solution added with mere distilled water in place of PQQ-GDH solution. The amount of enzyme which produces diformazan at ½ $\mu$M per min as measured by the above method was defined as one unit.

In the following, the present invention will be described more specifically by way of concrete examples. However, the present invention is not limited only to those examples.

EXAMPLES

FIG. 1 is a schematic plan view of a biosensor in accordance with one example of the present invention with an omission of the reaction layer.

As shown in the figure, a silver paste is printed on an electrically insulating base plate 1 made of polyethylene terephthalate using the known screen printing method in order to form leads 2 and 3. Then, a conductive carbon paste containing a resin binder is printed on the base plate 1 to form a working electrode 4. The working electrode 4 is in contact with the lead 2. The base plate 1 is further formed thereon with an insulating layer 6 by printing an insulating paste. The insulating layer 6 surrounds the periphery of the working electrode 4 to hold the exposed area of the working electrode 4 constant. Then, a ring-like counter electrode 5 is formed on the base plate 1 by printing the same conductive carbon paste containing a resin binder as above such that the paste has a contact with the lead 3.

Figure 2:
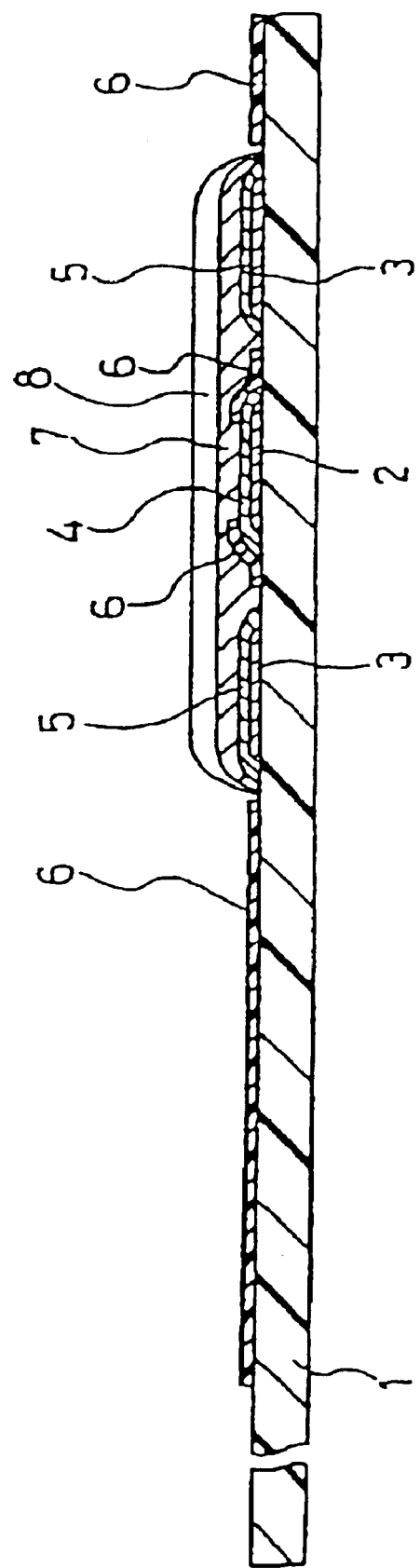
FIG. 2 is a longitudinal cross-sectional view illustrating the vital parts of the glucose sensor shown in FIG. 1.

FIG. 2 is a schematic longitudinal cross-sectional view of the biosensor of FIG. 1. On the base plate 1 as shown in FIG. 1, a hydrophilic polymer layer 7 of carboxymethyl cellulose is formed, on which a reaction layer 8 containing PQQ-GDH plus the additive is further formed.

Example 1

A 0.5 wt % aqueous sodium salt solution of a hydrophilic polymer, carboxymethyl cellulose (hereinafter abbreviated to "CMC"), was dropped on the electrode system on the base plate 1 in FIG. 1 and dried for 10 min in a warm air drier at 50° C. to form the CMC layer 7. Then, a mixed solution dissolving 5,000 U PQQ-GDH, 20 $\mu$M potassium hydrogen phthalate and 50 $\mu$M potassium ferricyanide in 1 ml water was dropped on the CMC layer 7 and dried to form the reaction layer 8. In this way, the glucose sensor of Example 1 was produced.

Then, aqueous solutions containing various concentrations of glucose were prepared as sample solutions. Each of the sample solutions thus prepared was dropped on the reaction layer 8. Upon supply of the glucose sample solution to the reaction layer, glucose contained in the sample solution was oxidized by PQQ-GDH present in the reaction layer 8. At that time, potassium ferricyanide in the reaction layer was reduced to potassium ferricyanide.

One minute after dropping the sample solution, a voltage of +0.5 V was applied onto the working electrode 4 using the counter electrode 5 as reference in order to reoxidize potassium ferrocyanide. Five seconds after voltage application, current flowing across the working and the counter electrodes 4 and 5 was measured.

Current values were obtained from all of the sample solutions containing various concentrations of glucose in the same manner as noted above. Finally, a graph showing response characteristics of the glucose sensor to the sample solutions was prepared by plotting the glucose concentration on the X axis and the current value on the Y axis. The results are shown in FIG. 3.

An identical biosensor was produced in the same manner as described above and preserved at room temperature for 6 months in order to prepare a graph showing its response characteristics after 6-month preservation. The results are also given in FIG. 3.

Figure 3:
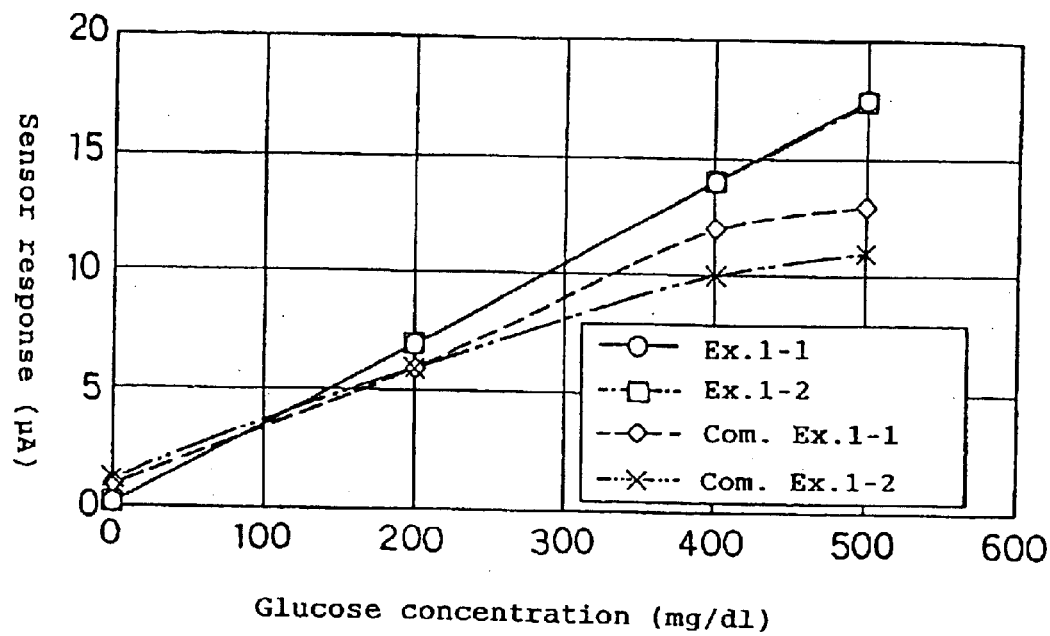
FIG. 3 is a graph illustrating response characteristics obtained from a glucose sensor in accordance with Example 1 of the present invention and those from a glucose sensor in accordance with Comparative Example 1.
Figure 4:
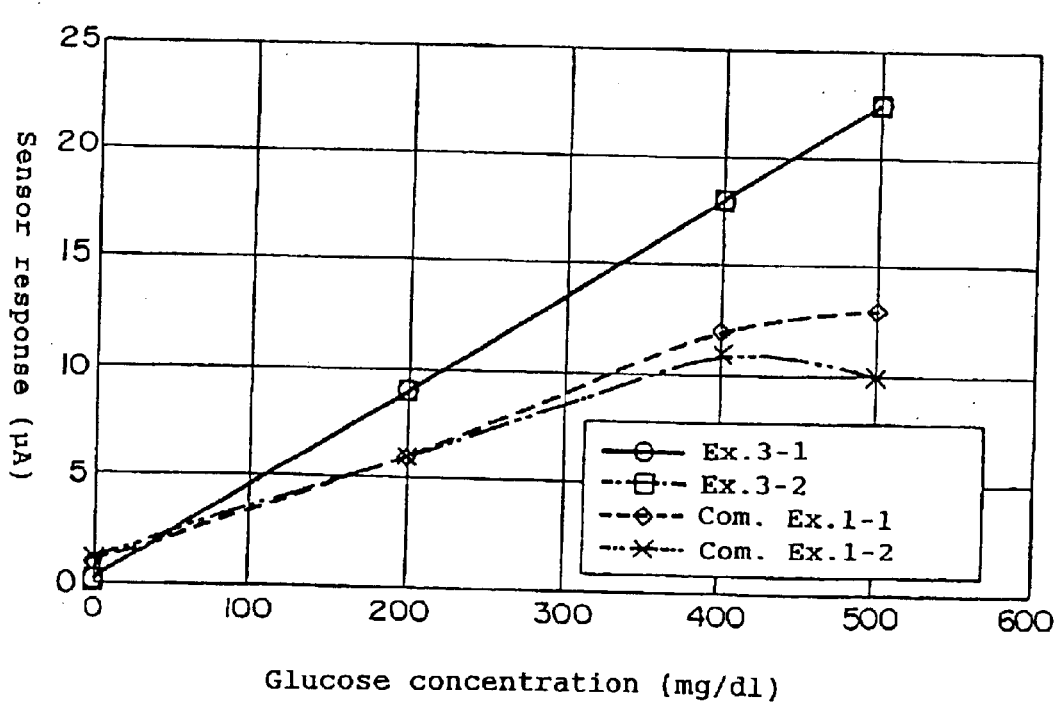
FIG. 4 is a graph illustrating response characteristics obtained from a glucose sensor in accordance with Example 3 of the present invention and those from the glucose sensor in accordance with Comparative Example 1.
Figure 5:
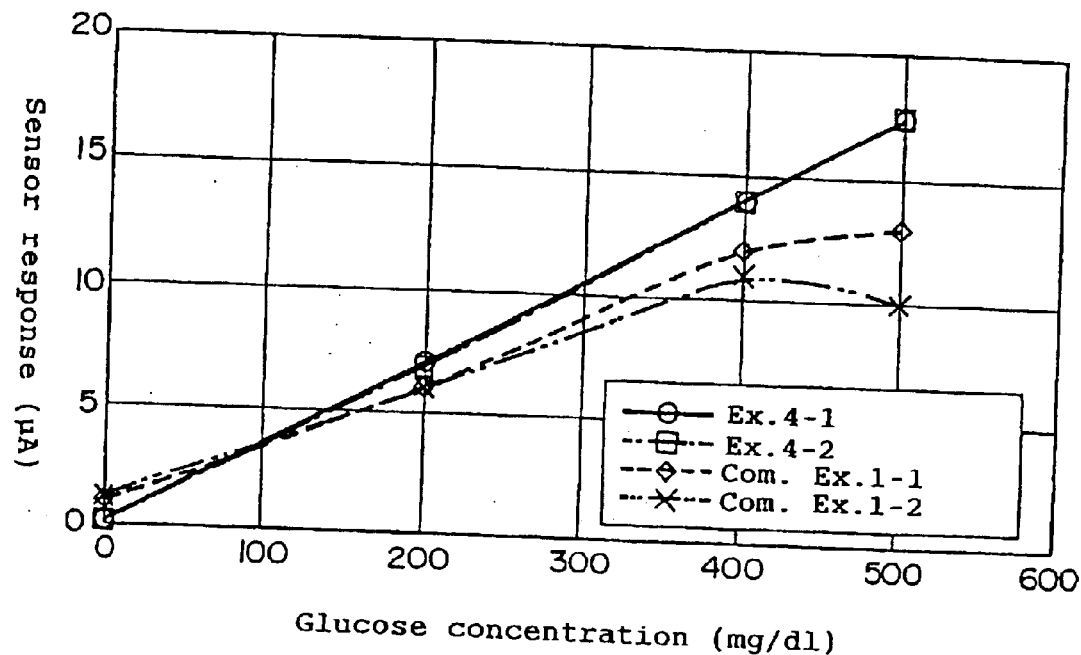
FIG. 5 is a graph illustrating response characteristics obtained from a glucose sensor in accordance with Example 4 of the present invention and those from the glucose sensor in accordance with Comparative Example 1.
Figure 6:
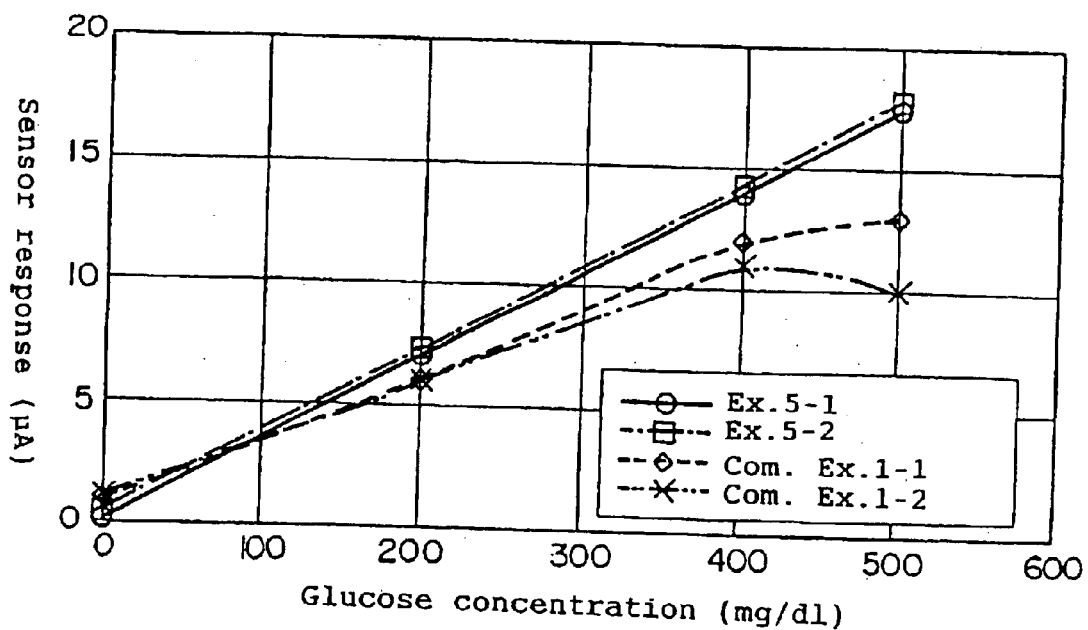
FIG. 6 is a graph illustrating response characteristics obtained from a glucose sensor in accordance with Example 5 of the present invention and those from the glucose sensor in accordance with Comparative Example 1.
Figure 7:
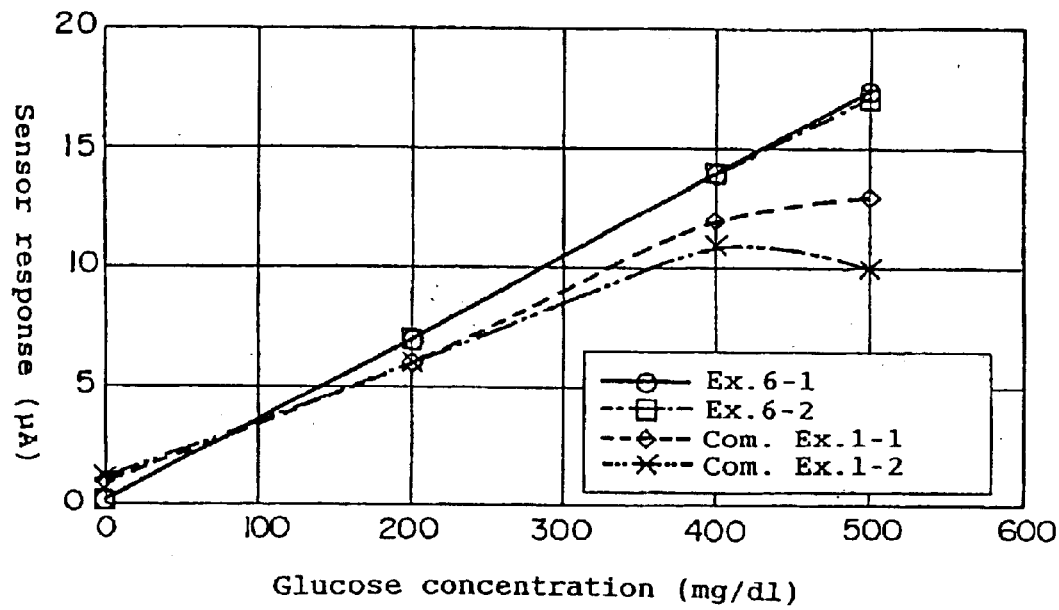
FIG. 7 is a graph illustrating response characteristics obtained from a glucose sensor in accordance with Example 6 of the present invention and those from the glucose sensor in accordance with Comparative Example 1.
Figure 8:
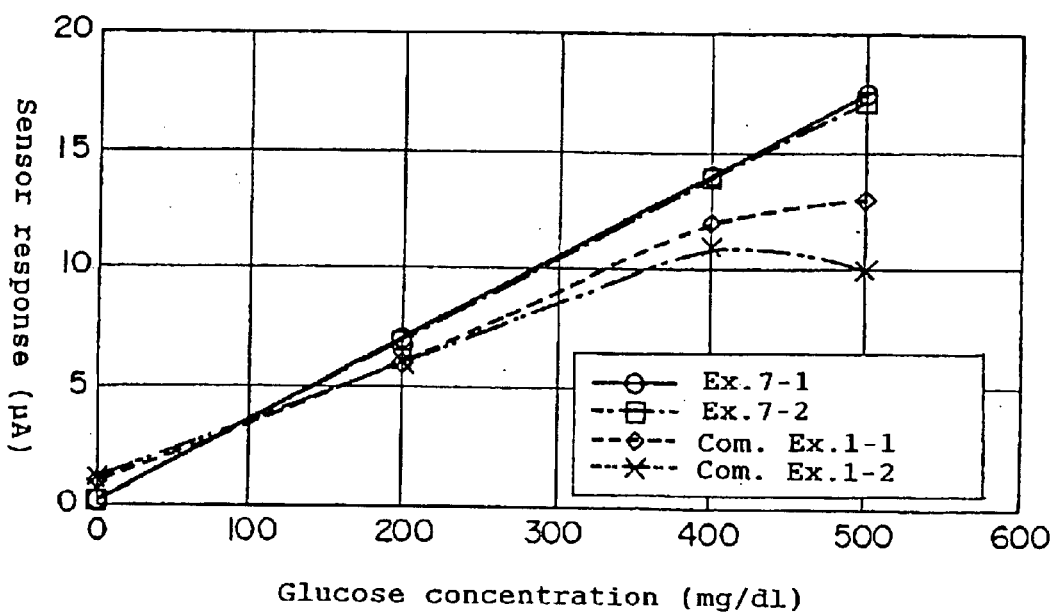
FIG. 8 is a graph illustrating response characteristics obtained from a glucose sensor in accordance with Example 7 of the present invention and those from the glucose sensor in accordance with Comparative Example 1.
Figure 9:
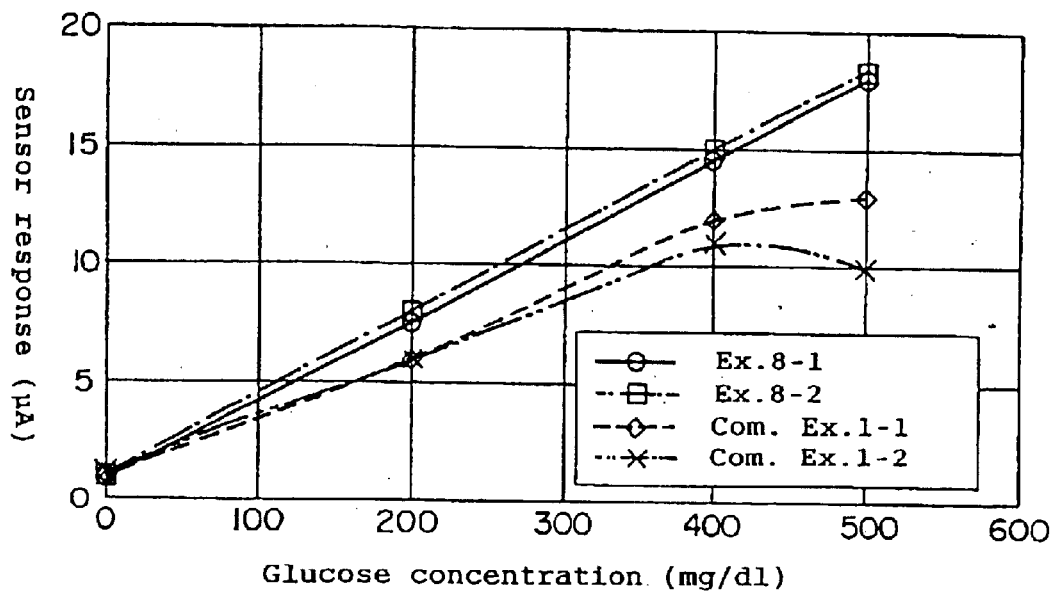
FIG. 9 is a graph illustrating response characteristics obtained from a glucose sensor in accordance with Example 8 of the present invention and those from the glucose sensor in accordance with Comparative Example 1.
Figure 10:
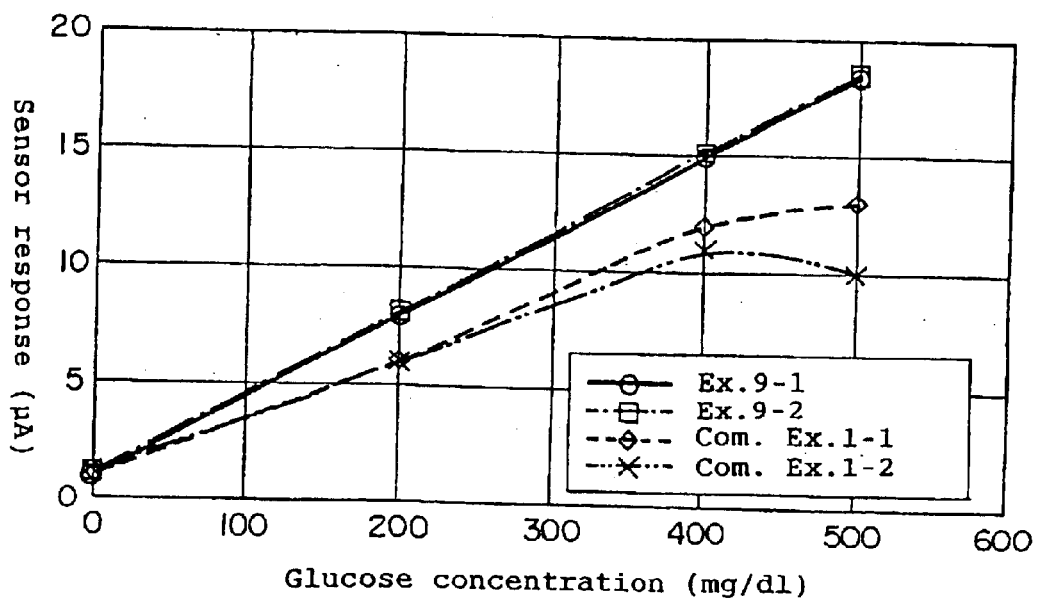
FIG. 10 is a graph illustrating response characteristics obtained from a glucose sensor in accordance with Example 9 of the present invention and those from the glucose sensor in accordance with Comparative Example 1.
Figure 11:
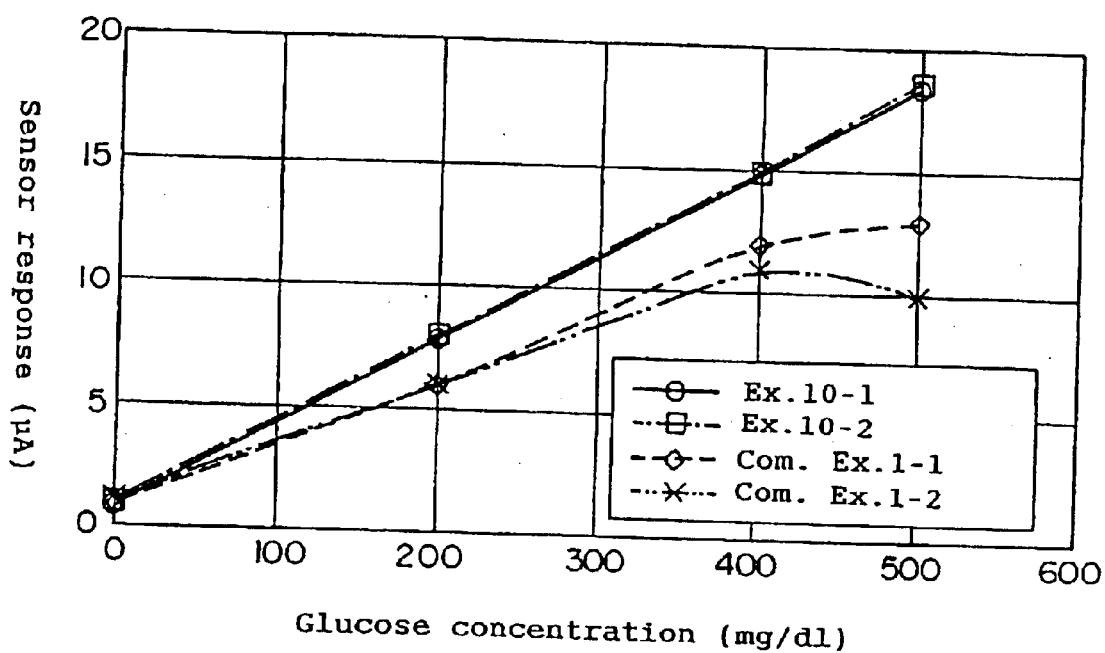
FIG. 11 is a graph illustrating response characteristics obtained from a glucose sensor in accordance with Example 10 of the present invention and those from the glucose sensor in accordance with Comparative Example 1.

As evident from FIG. 3, the biosensors of Example 1 produce an extremely low blank value. It is also noted that there is a certain correlation between the glucose concentration and the current value with sharp linearity.

The sensor response characteristics 6 months after production as shown by "Ex.1-2" were almost unchanged compared to those immediately after production as shown by "Ex.1-1". This indicates that the biosensors of Example 1 can well stand stable against preservation.

Comparative Example 1

Another glucose sensor was produced in the same manner as in Example 1, except for the use of potassium phosphate in place of potassium hydrogen phthalate. Then, a graph of sensor response characteristics immediately after production as shown by "Com.Ex.1-1" and after 6 month-preservation as shown by "Com.Ex.1-2" was prepared in the same manner as in Example 1. The results are shown in FIG. 3.

As apparent from FIG. 3, the glucose sensor of Comparative Example 1 produces a high blank value. The response current value of the sensor is higher than the real current value reflecting the glucose concentration when the glucose concentration in the sample solution is lower than 110 mg/dl. When the glucose concentration in the sample solution is higher than 110 mg/dl, the response current value is lower in the glucose sensor of Comparative Example 1 than that of Example 1. The linear correlation between the glucose concentration and the current value immediately after production is also lower.

The linear correlation further decreased after 6-month preservation compared to that immediately after production.

As such, the glucose sensor of Comparative Example 1 had poor preservation characteristics.

Comparative Example 2

Another glucose sensor was produced in the same manner as in Example 1, except for omission of potassium hydrogen phthalate. Then, a graph of response characteristics of the sensor immediately after production and after 6-month preservation was prepared in the same manner as in Example 1.

The results showed that the sensor of Comparative Example 2 produced a surprisingly high blank value and low increases in the current value in response to increases in the substrate concentration. The enzyme lost its enzyme activity after 6-month preservation of the sensor and there was almost no change in the current value in response to increased substrate concentrations.

Example 2

In this example, a glucose sensor was produced in the same manner as in Example 1, except for omission of the CMC layer 7 on the electrode system. Then, a graph of response characteristics of the sensor immediately after production and after 6-month preservation was prepared in the same manner as in Example 1.

The results showed a certain correlation between the glucose concentration and the current value with satisfactory linearity. The sensor was low in blank value. Moreover, the sensor response characteristics 6 months after production were almost unchanged compared to those immediately after production. This indicates satisfactory stability of the sensor of Example 2 against preservation.

Examples 3 to 10

In these examples, glucose sensors were produced in the same manner as in Example 1 by using maleic acid (Example 3), succinic acid (Example 4), triethanol amine hydrochloride (Example 5), sodium dihydrogen citrate (Example 6), dimethyl glutaric acid (Example 7), 2-(N-morpholino)ethane sulfonic acid (Example 8), tris (hydroxyethyl)glycine (Example 9) or tris(hydroxymethyl) aminomethane (Example 10) in place of potassium hydrogen phthalate. Then, graphs of response characteristics of the sensors immediately after production as shown by "Ex.3-1 to Ex.10-1" and after 6-month preservation as shown by "Ex.3-2 to Ex.10-2" were prepared in the same manner as in Example 1. The results obtained from the sensors are shown in FIG. 4 to FIG. 11.

FIG. 4 to FIG. 11 indicate very low blank values and a certain correlation between the glucose concentration and the current value. The sensors were highly responsive, demonstrating satisfactory linearity. Moreover, the sensor response characteristics 6 months after production were almost unchanged compared to those immediately after production. This indicates satisfactory stability of the sensors of Examples 3 to 10 against preservation.

Examples 11 to 18

In these examples, glucose sensors were produced in the same manner as in Examples 3 to 10, except for omission of the CMC layer 7 on the electrode system. Then, graphs of response characteristics of the sensors immediately after production and after 6-month preservation were prepared similarly.

The results indicate a certain correlation between the glucose concentration and the current value with satisfactory linearity. The blank value was also very low in all the sensors. Moreover, the sensor response characteristics 6 months after production were almost unchanged compared to those immediately after production. This indicates satisfactory stability of the sensors of Examples 11 to 18 against preservation.

Example 19

In this example, 10 U/ml of the PQQ-GDH in accordance with the present invention was dissolved in various additives (20 mM) each containing 1 mM calcium chloride (which will be called "buffer solutions") and stored at 37° C. for 3 days to examine the residual enzyme activity (more specifically, ratio of remaining enzyme activity of the PQQ-GDH to that immediately after being dissolved in either buffer solution). Calcium chloride was omitted when the buffer was potassium phosphate buffer solution.

Table 1 lists the residual enzyme activity of PQQ-GDH dissolved in the various buffer solutions.

TABLE 1

| Buffer solution | pH | Residual activity (%) |
| --- | --- | --- |
| Potassium hydrogen phthalate | 6.0 | 100 |
| Maleic acid | 6.5 | 100 |
| Succinic acid | 6.0 | 100 |
| Triethanol amine | 7.0 | 100 |
| Sodium dihydrogen citrate | 6.5 | 100 |
| Dimethyl glutaric acid | 6.5 | 100 |
| Tricine | 7.5 | 95.4 |
| Imidazole | 7.5 | 100 |
| Collidine | 6.5 | 96.1 |
| Tris hydrochloride | 7.5 | 63.4 |
| Potassium phosphate | 6.5 | 44.3 |

Table 1 indicates that all the additives in accordance with the present invention produce better stability than the conventional potassium phosphate buffer solution and tris hydrochloride buffer solution which are widely applied additives.

Example 20

In this example, the PQQ-GDH in accordance with the present invention was dissolved in a variety of additives containing 1 mM calcium chloride in addition to BSA (which will be called buffer solutions). The mixing ratio of BSA was 0.3 part by weight to 1.0 part by weight of PQQ-GDH. The solution thus prepared was lyophilized (=freeze-dried) and stored at 37° C. for 1 week to examine the residual enzyme activity (more specifically, ratio of remaining enzyme activity of the PQQ-GDH to that immediately after being dissolved in either buffer solution). The results are shown in Table 2.

TABLE 2

| Buffer solution | pH | Residual activity (%) |
| --- | --- | --- |
| Tris hydrochloride | 7.5 | 22.1 |
| Potassium phosphate | 6.5 | 66.2 |
| Potassium hydrogen phthalate | 6.0 | 83.2 |
| Maleic acid | 6.5 | 72.1 |
| Succinic acid | 6.0 | 80.5 |

Table 2 indicates that all the additives in accordance with the present invention are superior to the widely used conventional potassium phosphate buffer solution and tris hydrochloride buffer solution in securing stable activity of the enzyme composition prepared by a freeze-drying method.

As discussed above, the present invention can provide a high performance glucose sensor which well stands long-term preservation and has a low blank value. The present invention can also provide a glucose dehydrogenase composition bound with pyrrolo-quinoline quinone as coenzyme for use in glucose sensors, the composition being more stable than the conventional glucose dehydrogenase composition.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A glucose sensor comprising an electrically insulating base plate, an electrode system including at least a working electrode and a counter electrode formed on said base plate, and a reaction layer which is formed in contact with or in the vicinity of said electrode system,
   wherein said reaction layer contains phthalic acid or a phthalate, and a glucose dehydrogenase whose coenzyme is pyrrolo-quinoline quinone.

2. The glucose sensor in accordance with claim 1, wherein said reaction layer further contains a stabilizer, said stabilizer having a function of retaining the activity of the enzyme and the long-term preservation of said sensor and decreasing the blank value of said sensor.

3. The glucose sensor in accordance with claim 2, wherein said stabilizer is a metal salt, an organic acid, a protein, an amide acid, a sugar or a derivative thereof, a surfactant, or ammonium sulfate.

4. The glucose sensor in accordance with claim 3, wherein said stabilizer is a metal salt selected from the group consisting of a calcium salt, a strontium salt and a manganese salt.

5. The glucose sensor in accordance with claim 4, wherein said metal salt is a sulfate, a nitrate or a halide.

6. The glucose sensor in accordance with claim 4, wherein said calcium salt is $CaCl_2$.

7. The glucose sensor in accordance with claim 3, wherein said stabilizer is an organic acid selected from the group consisting of α-ketoglutaric acid, malic acid, fumaric acid, gluconic acid, cholic acid and deoxycholic acid.

8. The glucose sensor in accordance with claim 3, wherein said stabilizer is a protein selected from the group consisting of bovine serum albumin, egg albumin and gelatin.

9. The glucose sensor in accordance with claim 3, wherein said stabilizer is a sugar or a derivative thereof selected from the group consisting of a monosaccharide and a derivative thereof, a disaccharide and a derivative thereof, an oligosaccharide and a derivative thereof and a polysaccharide and a derivative thereof.

10. The glucose sensor in accordance with claim 9, wherein said stabilizer is a monosaccharide selected from the group consisting of glucose, fructose, galactose, mannose, xylose, inositol, monnitol, sorbitol, ribitol, glucosamine and deoxyglucose, or a derivative thereof.

11. The glucose sensor in accordance with claim 9, wherein said stabilizer is a disaccharide selected from the group consisting of sucrose, lactose, maltose and trehalose, or a derivative thereof.

12. The glucose sensor in accordance with claim 9, wherein said stabilizer is an oligosaccharide selected from the group consisting of malt triose, maltosyl cyclodextrin, α-cyclodextrin, β-cyclodextrin and γ-cyclodextrin, or a derivative thereof.

13. The glucose sensor in accordance with claim 9, wherein said stabilizer is a polysaccharide selected from the group consisting of dextrin, amylose, glycogen, inulin and Ficoll, or a derivative thereof.

14. The glucose sensor in accordance with claim 3, said stabilizer is an amido acid selected from the group consisting of lysine, histidine, glutamic acid, glycylglycine and polylysine.

15. The glucose sensor in accordance with claim 3, wherein said stabilizer is a non-ionic surfactant.

16. The glucose sensor in accordance with claim 1, wherein said reaction layer further contains maleic acid, a maleate, succinic acid, a succinate, triethanol amine, a triethanol amine salt, citric acid, a citrate, dimethyl glutaric acid, 2-(N-morpholino) ethane sulfonic acid, a 2-(N-morpholino)ethane sulfonate, tris(hydroxymethyl)glycine, a tris(hydroxymethyl)glycine salt, tris (hydroxymethyl) aminomethane, a tris(hydroxymethyl)aminomethane salt, imidazole or collidine.

17. A method for stabilizing glucose dehydrogenase for use in glucose sensors, wherein at least one additive is added to glucose dehydrogenase whose coenzyme is pyrrolo-quinoline quinone, said additive being selected from the group consisting of phthalic acid, a phthalate, triethanol amine, a triethanol amine salt, dimethyl glutaric acid, 2-(N-morpholino)ethane sulfonic acid, a 2-(N-morpholino)ethane sulfonate, tris(hydroxymethyl)glycine, a tris (hydroxymethyl)glycine salt, tris(hydroxymethyl) aminomethane, a tris(hydroxymethyl)aminomethane salt, imidazole and collidine.

18. A method for stabilizing glucose dehydrogenase for use in glucose sensors, said glucose sensors each having a reaction layer comprising a glucose-dehydrogenase whose coenzyme is pyrrolo-quinoline quinone, wherein phthalic acid or a phthalate is added to said glucose-dehydrogenase whose coenzyme is pyrrolo-quinoline quinone.

19. The method for stabilizing glucose dehydrogenase for use in glucose sensors in accordance with claim 18, wherein a stabilizer is added to said glucose dehydrogenase whose coenzyme is pyrrolo-quinoline quinone, said stabilizer having a function of retaining the activity of enzyme and the long-term preservation of said sensor and decreasing the blank value of said sensor.

20. The method for stabilizing glucose dehydrogenase for use in glucose sensors in accordance with claim 19, wherein said stabilizer is a metal salt, an organic acid, a protein, an amino acid, a sugar or a derivative thereof, a surfactant, or ammonium sulfate.

21. The method for stabilizing glucose dehydrogenase for use in glucose sensors in accordance with claim 20, wherein said stabilizer is a metal salt selected from the group consisting of a calcium salt, a strontium salt and a manganese salt.

22. The method for stabilizing glucose dehydrogenase for use in glucose sensors in accordance with claim 21, wherein said metal salt is a sulfate, a nitrate or a halide.

23. The method for stabilizing glucose dehydrogenase for use in glucose sensors in accordance with claim 21, wherein said calcium salt is $CaCl_2$.

24. The method for stabilizing glucose dehydrogenase for use in glucose sensors in accordance with claim 20, wherein said stabilizer is an organic acid selected from the group consisting of α-ketoglutaric acid, malic acid, fumaric acid, gluconic acid, cholic acid and deoxycholic acid.

25. The method for stabilizing glucose dehydrogenase for use in glucose sensors in accordance with claim 20, wherein said stabilizer is a protein selected from the group consisting of bovine serum albumin, egg albumin and gelatin.

26. The method for stabilizing glucose dehydrogenase for use in glucose sensors in accordance with claim 20, wherein said stabilizer is a sugar or a derivative thereof selected from the group consisting of a monosaccharide and a derivative thereof, a disaccharide and a derivative thereof, an oligosaccharide and a derivative thereof, and a polysaccharide and a derivative thereof.

27. The method for stabilizing glucose dehydrogenase for use in glucose sensors in accordance with claim 26, wherein said stabilizer is a monosaccharide selected from the group consisting of glucose, fructose, galactose, mannose, xylose, inositol, monnitol, sorbitol, ribitol, glucosamine and deoxyglucose, or a derivative thereof.

28. The method for stabilizing glucose dehydrogenase for use in glucose sensors in accordance with claim 26, wherein said stabilizer is a disaccharide selected from the group consisting of sucrose, lactose, maltose and trehalose, or a derivative thereof.

29. The method for stabilizing glucose dehydrogenase for use in glucose sensors in accordance with claim 26, wherein said stabilizer is an oligosaccharide selected from the group consisting of malt triose, maltosyl cyclodextrin, α-cyclodextrin, β-cyclodextrin and γ-cyclodextrin, or a derivative thereof.

30. The method for stabilizing glucose dehydrogenase for use in glucose sensors in accordance with claim 26, wherein said stabilizer is a polysaccharide selected from the group consisting of dextrin, amylose, glycogen, inulin and Ficoll, or a derivative thereof.

31. The method for stabilizing glucose dehydrogenase for use in glucose sensors in accordance with claim 20, wherein said stabilizer is an amino acid selected from the group consisting of lysine, histidine, glutamic acid, glycylglycine and polylysine.

32. The method for stabilizing glucose dehydrogenase for use in glucose sensors in accordance with claim 20, wherein said stabilizer is a non-ionic surfactant.

33. The method for stabilizing glucose dehydrogenase for use in glucose sensors in accordance with any of claim 18 to 32, wherein said reaction layer further contains maleic acid, a maleate, succinic acid, a succinate, triethanol amine, a triethanol amine salt, citric acid, a citrate, dimethyl glutaric acid, 2-(N-morpholino)ethane sulfonic acid, a 2-(N-morpholino)ethane sulfonate, tris(hydroxymethyl)glycine, a tris(hydroxymethyl)glycine salt, tris(hydroxymethyl) aminomethane, a tris(hydroxymethyl)aminomethane salt, imidazole or collidine.

34. A glucose dehydrogenase composition for use in glucose sensors, said composition containing glucose dehydrogenase whose coenzyme is pyrrolo-quinoline quinone, and at lease one additive selected from the group consisting of phthalic acid, a phthalate, triethanol amine, a triethanol amine salt, dimethyl glutaric acid, (N-morpholino)ethane sulfonic acid, a 2-(N-morpholino)ethane sulfonate tris (hydroxymethyl)glycine, a tris(hydroxymethyl)glycine salt, tris(hydroxymethyl)aminomethane, a tris(hydroxymethyl) aminomethane salt, imidazole and collidine.

35. A glucose dehydrogenase composition for use in glucose sensors, said composition containing glucose dehydrogenase whose coenzyme is pyrrolo-quinoline quinone, and phthalic acid or a phthalate.

36. The glucose dehydrogenase composition for use in glucose sensors in accordance with claim 35, said composition further containing a stabilizer, said stabilizer having a function of retaining the activity of the enzyme and the long-term preservation of said sensor and decreasing the blank value of said sensor.

37. The glucose dehydrogenase composition for use in glucose sensors in accordance with claim 36, wherein said stabilizer is a metal salt, an organic acid, a protein, an amino acid, a sugar or a derivative thereof, a surfactant, or ammonium sulfate.

38. The glucose dehydrogenase composition for use in glucose sensors in accordance with claim 37, wherein said stabilizer is a metal salt selected from the group consisting of a calcium salt, a strontium salt and a manganese salt.

39. The glucose dehydrogenase composition for use in glucose sensors in accordance with claim 38, wherein said metal salt is a sulfate, a nitrate or a halide.

40. The glucose dehydrogenase composition for use in glucose sensors in accordance with claim 38, wherein said calcium salt is $CaCl_2$.

41. The glucose dehydrogenase composition for use in glucose sensors in accordance with claim 37, wherein said stabilizer is an organic acid selected from the group consisting of a α-ketoglutaric acid, malic acid, fumaric acid, gluconic acid, cholic acid and deoxycholic acid.

42. The glucose dehydrogenase composition for use in glucose sensors in accordance with claim 37, wherein said stabilizer is a protein selected from the group consisting of bovine serum albumin, egg albumin and gelatin.

43. The glucose dehydrogenase composition for use in glucose sensors in accordance with claim 37, wherein said stabilizer is a sugar or a derivative thereof selected from the group consisting of a monosaccharide and a derivative thereof, a disaccharide and a derivative thereof, an oligosaccharide and a derivative thereof, and a polysaccharide and a derivative thereof.

44. The glucose dehydrogenase composition for use in glucose sensors in accordance with claim 43, wherein said stabilizer is a monosaccharide selected from the group consisting of glucose, fructose, galactose, mannose, xylose, inositol, monnitol, sorbitol, ribitol glucosamine and deoxyglucose, or a derivative thereof.

45. The glucose dehydrogenase composition for use in glucose sensors in accordance with claim 43, wherein said stabilizer is a disaccharide selected from the group consisting of sucrose, lactose, maltose and trehalose, or a derivative thereof.

46. The glucose dehydrogenase composition for use in glucose sensors in accordance with claim 43, wherein said stabilizer is an oligosaccharide selected from the group consisting of malt triose, maltosyl cyclodextrin, α-cyclodextrin, β-cyclodextrin and γ-cyclodextrin, or a derivative thereof.

47. The glucose dehydrogenase composition for use in glucose sensors in accordance with claim 43, wherein said stabilizer is a polysaccharide selected from the group consisting of dextrin, amylose, glycogen, inulin and Ficoll, or a derivative thereof.

48. The glucose dehydrogenase composition for use in glucose sensors in accordance with claim 37, said stabilizer is an amino acid selected from the group consisting of lysine, histidine, glutamic acid, glycylglycine and polylysine.

49. The glucose dehydrogenase composition for use in glucose sensors in accordance with claim 37, wherein said stabilizer is a non-ionic surfactant.

50. The glucose dehydrogenase composition for use in glucose sensors in accordance with any of claims 35 to 49, wherein said composition further contains maleic acid, a maleate, succinic acid, a succinate, triethanol amine, a triethanol amine salt, citric acid, a citrate, dimethyl glutaric acid, 2-(N-morpholino)ethane sulfonic acid, a 2-(N-morpholino)ethane sulfonate, tris(hydroxymethyl)glycine, a tris(hydroxymethyl)glycine salt, tris(hydroxymethyl) aminomethane, a tris(hydroxymethyl)aminomethane salt, imidazole or collidine.

51. A glucose sensor comprising an electrically insulating base plate, an electrode system including at least a working electrode and a counter electrode formed on said base plate, and a reaction layer which is formed in contact with or in the vicinity of said electrode system wherein said reaction layer contains: a glucose dehydrogenase whose coenzyme is pyrrolo-quinoline quinone; and an additive selected from the group consisting of triethanol amine, a triethanol amine salt, citric acid, a citrate, dimethyl glutaric acid, 2-(N-morpholino)ethane sulfonic acid, a 2-(N-morpholino)ethane sulfonate, tris(hydroxymethyl)glycine, a tris (hydroxymethyl)glycine salt, tris(hydroxymethyl) aminomethane, a tris(hydroxymethyl)aminomethane salt, imidazole and collidine.

52. The glucose sensor in accordance with claim 51, further comprising a at least one stabilizer selected from the group consisting of a metal salt, an organic acid, a protein, and a sugar and a derivative thereof.

53. The glucose sensor in accordance with claim 51, wherein the response of the sensor to glucose within the concentration range of 0 to 500 mg/dl is substantially linear after long term preservation.

54. A method for stabilizing glucose dehydrogenase for use in glucose sensors, wherein a stabilizer and a buffer are added to glucose dehydrogenase whose coenzyme is pyrrolo-quinoline quinone, said stabilizer being selected from the group consisting of a metal salt, an organic acid, a protein, and a sugar and a derivative thereof, and said buffer being selected from the group consisting of maleic acid, a maleate, triethanol amine, a triethanol amine salt, dimethyl glutaric acid, 2-(N-morpholino)ethane sulfonic acid, a 2-(N-morpholino)ethane sulfonate, tris(hydroxymethyl) glycine, a tris(hydroxymethyl)glycine salt, tris (hydroxymethyl)aminomethane, a tris(hydroxymethyl) aminomethane salt, imidazole and collidine.

55. The method for stabilizing glucose dehydrogenase for use in glucose sensors in accordance with claim 54, wherein said stabilizer is a metal salt selected from the group consisting of a calcium salt, $CaCl_2$, a strontium salt and a manganese salt.

56. The method for stabilizing glucose dehydrogenase for use in glucose sensors in accordance with claim 54, wherein said stabilizer is an organic acid selected from the group consisting of α-ketoglutaric acid, malic acid, fumaric acid, gluconic acid, cholic acid and deoxycholic acid.

57. The method for stabilizing glucose dehydrogenase for use in glucose sensors in accordance with claim 54, wherein said stabilizer is a protein selected from the group consisting of bovine serum albumin, egg albumin and gelatin.

58. The method for stabilizing glucose dehydrogenase for use in glucose sensors in accordance with claim 54, wherein said stabilizer is a sugar or a derivative thereof selected from the group consisting of a monosaccharide and a derivative thereof, a disaccharide and a derivative thereof, an oligosaccharide and a derivative thereof, and a polysaccharide and a derivative thereof.

59. The method for stabilizing glucose dehydrogenase for use in glucose sensors in accordance with claim 58, wherein said stabilizer is a monosaccharide selected from the group consisting of glucose, fructose, galactose, mannose, xylose, inositol, monnitol, sorbitol, ribitol, glucosamine and deoxyglucose, or a derivative thereof.

60. The method for stabilizing glucose dehydrogenase for use in glucose sensors in accordance with claim 58, wherein said stabilizer is a disaccharide selected from the group consisting of sucrose, lactose, maltose and trehalose, or a derivative thereof.

61. The method for stabilizing glucose dehydrogenase for use in glucose sensors in accordance with claim 58, wherein said stabilizer is an oligosaccharide selected from the group consisting of malt triose, maltosyl cyclodextrin, α-cyclodextrin, β-cyclodextrin and γ-cyclodextrin, or a derivative thereof.

62. The method for stabilizing glucose dehydrogenase for use in glucose sensors in accordance with claim 58, wherein said stabilizer is a polysaccharide selected from the group consisting of dextrin, amylose, glycogen, inulin and Ficoll, or a derivative thereof.

63. A glucose dehydrogenase composition for use in glucose sensors, said composition containing: at least one stabilizer selected from the group consisting of a metal salt, an organic acid, a protein, and a sugar and a derivative thereof; a glucose dehydrogenase whose coenzyme is pyrrolo-quinoline quinone; and a buffer selected from the group consisting of maleic acid, a maleate, triethanol amine, a triethanol amine salt, dimethyl glutaric acid, 2-(N-morpholino)ethane sulfonic acid, a 2-(N-morpholino)ethane sulfonate, tris(hydroxymethyl)glycine, a tris (hydroxymethyl)glycine salt, tris(hydroxymethyl) aminomethane, a tris(hydroxymethyl)aminomethane salt, imidazole and collidine.

64. The glucose dehydrogenase composition for use in glucose sensors in accordance with claim 63, wherein said stabilizer is a metal salt selected from the group consisting of a calcium salt, $CaCl_2$, a strontium salt and a manganese salt.

65. The glucose dehydrogenase composition for use in glucose sensors in accordance with claim 63, wherein said stabilizer is an organic acid selected from the group consisting of α-ketoglutaric acid, malic acid, fumaric acid, gluconic acid, cholic acid and deoxycholic acid.

66. The glucose dehydrogenase composition for use in glucose sensors in accordance with claim 63, wherein said stabilizer is a protein selected from the group consisting of bovine serum albumin, egg albumin and gelatin.

67. The glucose dehydrogenase composition for use in glucose sensors in accordance with claim 63, wherein said stabilizer is a sugar or a derivative thereof selected from the group consisting of a monosaccharide and a derivative thereof, a disaccharide and a derivative thereof, an oligosaccharide and a derivative thereof, and a polysaccharide and a derivative thereof.

68. The glucose dehydrogenase composition for use in glucose sensors in accordance with claim 67, wherein said stabilizer is a monosaccharide selected from the group consisting of glucose, fructose, galactose, mannose, xylose, inositol, monnitol, sorbitol, ribitol, glucosamine and deoxyglucose, or a derivative thereof.

69. The glucose dehydrogenase composition for use in glucose sensors in accordance with claim 67, wherein said stabilizer is a disaccharide selected from the group consisting of sucrose, lactose, maltose and trehalose, or a derivative thereof.

70. The glucose dehydrogenase composition for use in glucose sensors in accordance with claim 67, wherein said stabilizer is an oligosaccharide selected from the group consisting of malt triose, maltosyl cyclodextrin, α-cyclodextrin, β-cyclodextrin and γ-cyclodextrin, or a derivative thereof.

71. The glucose dehydrogenase composition for use in glucose sensors in accordance with claim 67, wherein said stabilizer is a polysaccharide selected from the group consisting of dextrin, amylose, glycogen, inulin and Ficoll, or a derivative thereof.

72. A glucose sensor comprising an electrically insulating base plate, an electrode system including at least a working electrode and a counter electrode formed on said base plate, and a reaction layer which is formed in contact with or in the vicinity of said electrode system wherein said reaction layer contains: at least one stabilizer selected from the group consisting of a metal salt, an organic acid, a protein, and a sugar and a derivative thereof; a glucose dehydrogenase whose coenzyme is pyrrolo-quinoline quinone; and an additive selected from the group consisting of maleic acid, a maleate, triethanol amine, a triethanol amine salt, citric acid, a citrate, dimethyl glutaric acid, 2-(N-morpholino)ethane sulfonic acid, a 2-(N-morpholino)ethane sulfonate, tris(hydroxymethyl)glycine, a tris(hydroxymethyl)glycine salt, tris(hydroxymethyl)aminomethane, a tris(hydroxymethyl)aminomethane salt, imidazole and collidine.

73. The glucose sensor in accordance with claim 72, wherein said stabilizer is a metal salt selected from the group consisting of a calcium salt, $CaCl_2$, a strontium salt and a manganese salt.

74. The glucose sensor in accordance with claim 72, wherein said stabilizer is an organic acid selected from the group consisting of α-ketoglutaric acid, malic acid, fumaric acid, gluconic acid, cholic acid and deoxycholic acid.

75. The glucose sensor in accordance with claim 72, wherein said stabilizer is a protein selected from the group consisting of bovine serum albumin, egg albumin and gelatin.

76. The glucose sensor in accordance with claim 72, wherein said stabilizer is a sugar or a derivative thereof selected from the group consisting of a monosaccharide and a derivative thereof, a disaccharide, and a derivative thereof, an oligosaccharide and a derivative thereof, and a polysaccharide and a derivative thereof.

77. The glucose sensor in accordance with claim 72, wherein said stabilizer is a monosaccharide selected from the group consisting of glucose, fructose, galactose, mannose, xylose, inositol, monnitol, sorbitol, ribitol, glucosamine and deoxyglucose, or a derivative thereof.

78. The glucose sensor in accordance with claim 72, wherein said stabilizer is a disaccharide selected from the group consisting of sucrose, lactose, maltose and trehalose, or a derivative thereof.

79. The glucose sensor in accordance with claim 72, wherein said stabilizer is an oligosaccharide selected from the group consisting of malt triose, maltosyl cyclodextrin, α-cyclodextrin, β-cyclodextrin and γ-cyclodextrin, or a derivative thereof.

80. The glucose sensor in accordance with claim 72, wherein said stabilizer is a polysaccharide selected from the group consisting of dextrin, amylose, glycogen, inulin and Ficoll, or a derivative thereof.

* * * * *

UNITED STATES PATENT AND TRADEMARK OFFICE
CERTIFICATE OF CORRECTION

PATENT NO. : 6,773,564 B1
DATED : August 10, 2004
INVENTOR(S) : Keiko Yugawa et al.

It is certified that error appears in the above-identified patent and that said Letters Patent is hereby corrected as shown below:

Title page,
Item [56], References Cited, OTHER PUBLICATIONS, "Dyah Iswantini et al," reference, change the cited pages from "245-254" to -- 249-254 --.
Add the following references:
-- Toshihikio YOSHIOKA et al., Disposable Biosensor Based on Bioelectrochemistry, National Technical Report Vol. 42, No. 2, Apr. 1996, pp. 71-75.

Koji Sode, Satoshi Nakasono, Mitsuharu Tanaka and Tadashi Matsunaga, Subzero Temperature Operating Biosensor Utilizing an Organic Solvent and Quinoprotein Glucose Dehydrogenase, 1993, Biotechnology and Bioengineering, Vol. 42, pp. 251-254.

Asteriani R. Dewanti and Johannis A. Duine, $Ca^{2+}$-Assisted, Direct Hydride Transfer, and Rate-Determining Tautomerization of C5-Reduced PQQ to $PQQH_2$ in the Oxidation of β-D-Glucose by Soluble, Quinoprotein Glucose Dehydrogenase, 2000, Biochemistry 2000, Vol. 39, pp. 9384-9392. --.

Signed and Sealed this

Nineteenth Day of April, 2005

JON W. DUDAS
*Director of the United States Patent and Trademark Office*